(12) United States Patent
Felsinger et al.

(10) Patent No.: US 11,034,831 B2
(45) Date of Patent: *Jun. 15, 2021

(54) SYNTHETIC TISSUE STRUCTURES FOR ELECTROSURGICAL TRAINING AND SIMULATION

(71) Applicant: Applied Medical Resources Corporation, Rancho Santa Margarita, CA (US)

(72) Inventors: Natasha Felsinger, Rancho Santa Margarita, CA (US); Sam Chehayeb, Lake Forest, CA (US); Eduardo Bolanos, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 280 days.

This patent is subject to a terminal disclaimer.

(21) Appl. No.: 16/138,652

(22) Filed: Sep. 21, 2018

(65) Prior Publication Data
US 2019/0085162 A1    Mar. 21, 2019

Related U.S. Application Data

(63) Continuation of application No. 15/208,873, filed on Jul. 13, 2016, now Pat. No. 10,081,727, which is a
(Continued)

(51) Int. Cl.
*G09B 23/30* (2006.01)
*C08L 33/26* (2006.01)
(Continued)

(52) U.S. Cl.
CPC ............ *C08L 33/26* (2013.01); *B29C 39/003* (2013.01); *C08J 5/122* (2013.01); *G09B 23/30* (2013.01);
(Continued)

(58) Field of Classification Search
CPC ................................ G09B 23/28; G09B 23/30
(Continued)

(56) References Cited

U.S. PATENT DOCUMENTS

| 184,573 A | 11/1876 | Becker |
|---|---|---|
| 2,127,774 A | 8/1938 | Jacobs |

(Continued)

FOREIGN PATENT DOCUMENTS

| CA | 2 293 585 A1 | 12/1998 |
|---|---|---|
| CN | 2421706 Y | 2/2001 |

(Continued)

OTHER PUBLICATIONS

Society of Laparoendoscopic Surgeons, "Future Technology Session: The Edge of Innovation in Surgery, Space, and Business," http://www.laparoscopytoday.com/endourology/page/2/ , Figure 1 B: http://laparoscopy.blogs.com/laparoscopy_today/images/6-1/6-1VlaovicPicB.jpg. Sep. 5-8, 2007, 10 pgs.

(Continued)

*Primary Examiner* — Kurt Fernstrom
(74) *Attorney, Agent, or Firm* — Patrick Ikehara

(57) ABSTRACT

A surgical simulator for electrosurgical training and simulation is provided. The surgical simulator includes one or more simulated tissue structures made substantially of a hydrogel comprising a dual interpenetrating network of ionically cross-linked alginate and covalently cross-linked acrylamide. Combinations of different simulated tissue structures define procedural-based models for the practice of various electrosurgical procedures including laparoscopic total mesorectal excision, transanal total mesorectal excision, cholecystectomy and transanal minimally invasive surgery. Methods of making the simulated tissue structures are also provided.

20 Claims, 4 Drawing Sheets

Related U.S. Application Data continuation of application No. PCT/US2016/032292, filed on May 13, 2016.

(60) Provisional application No. 62/161,322, filed on May 14, 2015, provisional application No. 62/257,877, filed on Nov. 20, 2015.

(51) Int. Cl.
    *C08J 5/12*     (2006.01)
    *B29C 39/00*     (2006.01)
    *B29K 33/00*     (2006.01)
    *A61B 18/12*     (2006.01)

(52) U.S. Cl.
    CPC ........... *A61B 18/12* (2013.01); *B29K 2005/00* (2013.01); *B29K 2033/26* (2013.01); *C08J 2333/26* (2013.01); *C08J 2405/04* (2013.01)

(58) Field of Classification Search
    USPC ................................ 434/262, 267, 268, 272
    See application file for complete search history.

(56) References Cited

U.S. PATENT DOCUMENTS

| | | |
|---|---|---|
| 2,284,888 A | 6/1942 | Arneil, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A | 11/1984 | Graham et al. |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Fracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,271,278 B1 | 8/2001 | Park et al. |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,589,057 B1 | 7/2003 | Keenan et al. |
| 6,620,174 B2 | 9/2003 | Jensen et al. |
| 6,654,000 B2 | 11/2003 | Rosenberg |
| 6,659,776 B1 | 12/2003 | Aumann et al. |
| 6,773,263 B2 | 8/2004 | Nicholls et al. |
| 6,780,016 B1 | 8/2004 | Toly |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |
| 7,621,749 B2 | 11/2009 | Munday |
| 7,646,901 B2 | 1/2010 | Murphy et al. |

(56) References Cited

U.S. PATENT DOCUMENTS

| | | |
|---|---|---|
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |
| 7,833,018 B2 | 11/2010 | Alexander et al. |
| 7,837,473 B2 | 11/2010 | Koh |
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,017,107 B2 | 9/2011 | Thomas et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,465,771 B2 | 6/2013 | Wan et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsooun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,690,580 B2 | 4/2014 | Paronen |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,096,744 B2 | 8/2015 | Wan et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,351,714 B2 | 5/2016 | Ross et al. |
| 9,336,694 B2 | 6/2016 | Shim et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,387,276 B2 | 7/2016 | Sun et al. |
| 9,427,496 B2 | 8/2016 | Sun et al. |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0126746 A1 | 7/2004 | Toly |
| 2004/0248072 A1 | 12/2004 | Gray et al. |
| 2005/0008997 A1 | 1/2005 | Herman |
| 2005/0026125 A1 | 2/2005 | Toly |
| 2005/0064378 A1 | 3/2005 | Toly |
| 2005/0084833 A1 | 4/2005 | Lacey et al. |
| 2005/0131390 A1 | 6/2005 | Heinrich et al. |
| 2005/0142525 A1 | 6/2005 | Cotin et al. |
| 2005/0192595 A1 | 9/2005 | Green et al. |
| 2005/0196739 A1 | 9/2005 | Moriyama |
| 2005/0196740 A1 | 9/2005 | Moriyama |
| 2005/0214727 A1 | 9/2005 | Stoianovici et al. |
| 2006/0046235 A1 | 3/2006 | Alexander et al. |
| 2006/0252019 A1 | 11/2006 | Burkitt et al. |
| 2006/0275741 A1 | 12/2006 | Chewning et al. |
| 2007/0074584 A1 | 4/2007 | Talarico et al. |
| 2007/0077544 A1 | 4/2007 | Lemperle et al. |
| 2007/0078484 A1 | 4/2007 | Talarico et al. |
| 2007/0148626 A1 | 6/2007 | Ikeda |
| 2007/0166682 A1 | 7/2007 | Yarin et al. |
| 2007/0197895 A1 | 8/2007 | Nycz et al. |

(56) References Cited

U.S. PATENT DOCUMENTS

| | | |
|---|---|---|
| 2007/0225734 A1 | 9/2007 | Bell et al. |
| 2007/0275359 A1 | 11/2007 | Rotnes et al. |
| 2008/0032272 A1 | 2/2008 | Palakodeti |
| 2008/0032273 A1 | 2/2008 | MacNamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0187895 A1 | 8/2008 | Sakezles |
| 2008/0188948 A1 | 8/2008 | Flatt |
| 2008/0299529 A1 | 12/2008 | Schaller |
| 2008/0317818 A1 | 12/2008 | Griffith et al. |
| 2009/0068627 A1 | 3/2009 | Toly |
| 2009/0142739 A1 | 6/2009 | Wang et al. |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0246747 A1 | 10/2009 | Buckman, Jr. |
| 2009/0298034 A1 | 12/2009 | Parry et al. |
| 2009/0314550 A1 | 12/2009 | Layton |
| 2010/0047752 A1 | 2/2010 | Chan et al. |
| 2010/0094312 A1 | 4/2010 | Ruiz Morales et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0167254 A1 | 7/2010 | Nguyen |
| 2010/0196867 A1 | 8/2010 | Geerligs et al. |
| 2010/0204713 A1 | 8/2010 | Ruiz Morales |
| 2010/0209899 A1 | 8/2010 | Park |
| 2010/0248200 A1 | 9/2010 | Ladak |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0285094 A1 | 11/2010 | Gupta |
| 2010/0324541 A1 | 12/2010 | Whitman |
| 2011/0020779 A1 | 1/2011 | Hannaford et al. |
| 2011/0046637 A1 | 2/2011 | Patel et al. |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Okano et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1 | 3/2014 | Tracy et al. |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0170623 A1 | 6/2014 | Jarstad et al. |
| 2014/0186809 A1 | 7/2014 | Hendrickson et al. |
| 2014/0187855 A1 | 7/2014 | Nagale et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1 | 9/2014 | Hart et al. |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |
| 2015/0135832 A1 | 5/2015 | Blumenkranz et al. |
| 2015/0148660 A1 | 5/2015 | Weiss et al. |
| 2015/0164598 A1 | 6/2015 | Blumenkranz et al. |
| 2015/0187229 A1 | 7/2015 | Wachli et al. |
| 2015/0194075 A1 | 7/2015 | Rappel et al. |
| 2015/0202299 A1 | 7/2015 | Burdick et al. |
| 2015/0209035 A1 | 7/2015 | Zemlock |

(56) References Cited

U.S. PATENT DOCUMENTS

| | | |
|---|---|---|
| 2015/0209059 A1 | 7/2015 | Trees et al. |
| 2015/0209573 A1 | 7/2015 | Hibner et al. |
| 2015/0228206 A1 | 8/2015 | Shim et al. |
| 2015/0262511 A1 | 9/2015 | Lin et al. |
| 2015/0265431 A1 | 9/2015 | Egilsson et al. |
| 2015/0272571 A1 | 10/2015 | Leimbach et al. |
| 2015/0272574 A1 | 10/2015 | Leimbach et al. |
| 2015/0272580 A1 | 10/2015 | Leimbach et al. |
| 2015/0272581 A1 | 10/2015 | Leimbach et al. |
| 2015/0272583 A1 | 10/2015 | Leimbach et al. |
| 2015/0272604 A1 | 10/2015 | Chowaniec et al. |
| 2015/0332609 A1 | 11/2015 | Alexander |
| 2015/0358426 A1 | 12/2015 | Kimball et al. |
| 2015/0371560 A1 | 12/2015 | Lowe |
| 2015/0374378 A1 | 12/2015 | Giordano et al. |
| 2015/0374449 A1 | 12/2015 | Chowaniec et al. |
| 2016/0000437 A1 | 1/2016 | Giordano et al. |
| 2016/0022374 A1 | 1/2016 | Haider et al. |
| 2016/0030240 A1 | 2/2016 | Gonenc et al. |
| 2016/0031091 A1 | 2/2016 | Popovic et al. |
| 2016/0058534 A1 | 3/2016 | Derwin et al. |
| 2016/0066909 A1 | 3/2016 | Baber et al. |
| 2016/0070436 A1 | 3/2016 | Thomas et al. |
| 2016/0073928 A1 | 3/2016 | Soper et al. |
| 2016/0074103 A1 | 3/2016 | Sartor |
| 2016/0098933 A1 | 4/2016 | Reiley et al. |
| 2016/0104394 A1 | 4/2016 | Miyazaki |
| 2016/0117956 A1 | 4/2016 | Larsson et al. |
| 2016/0125762 A1 | 5/2016 | Becker et al. |
| 2016/0133158 A1 | 5/2016 | Sui et al. |
| 2016/0140876 A1 | 5/2016 | Jabbour et al. |
| 2016/0194378 A1 | 7/2016 | Cass et al. |
| 2016/0199059 A1 | 7/2016 | Shelton, IV et al. |
| 2016/0220150 A1 | 8/2016 | Sharonov |
| 2016/0220314 A1 | 8/2016 | Huelman et al. |
| 2016/0225288 A1 | 8/2016 | East et al. |
| 2016/0232819 A1 | 8/2016 | Hofstetter et al. |
| 2016/0235494 A1 | 8/2016 | Shelton, IV et al. |
| 2016/0256187 A1 | 9/2016 | Shelton, IV et al. |
| 2016/0256229 A1 | 9/2016 | Morgan et al. |
| 2016/0262736 A1 | 9/2016 | Ross et al. |
| 2016/0262745 A1 | 9/2016 | Morgan et al. |
| 2016/0293055 A1 | 10/2016 | Hofstetter |
| 2016/0296144 A1 | 10/2016 | Gaddam et al. |
| 2017/0186340 A1* | 6/2017 | Ogawa .................... B32B 5/245 |
| 2018/0240366 A1* | 8/2018 | Felsinger ................ G09B 23/30 |

FOREIGN PATENT DOCUMENTS

| | | |
|---|---|---|
| CN | 2751372 Y | 1/2006 |
| CN | 2909427 Y | 6/2007 |
| CN | 101313842 A | 12/2008 |
| CN | 101528780 A | 9/2009 |
| CN | 201364679 Y | 12/2009 |
| CN | 201955979 U | 8/2011 |
| CN | 102458496 A | 5/2012 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 102596275 B | 6/2014 |
| CN | 103845757 A | 6/2014 |
| CN | 103886797 A | 6/2014 |
| CN | 103396562 B | 7/2015 |
| CN | 105194740 A | 12/2015 |
| CN | 105504166 A | 4/2016 |
| DE | 91 02 218 U1 | 5/1991 |
| DE | 41 05 892 A1 | 8/1992 |
| DE | 44 14 832 A1 | 11/1995 |
| DE | 19716341 A1 | 9/2000 |
| EP | 1 024 173 A1 | 8/2000 |
| EP | 1 609 431 A1 | 12/2005 |
| EP | 2 068 295 A2 | 6/2009 |
| EP | 2 218 570 A1 | 8/2010 |
| FR | 2 691 826 A1 | 12/1993 |
| FR | 2 917 876 A1 | 12/2008 |
| GB | 2488994 A | 9/2012 |
| JP | 10 211160 A | 8/1998 |
| JP | 2001005378 A | 1/2001 |
| JP | 2006187566 A | 7/2006 |
| JP | 2009063787 A | 3/2009 |
| JP | 2009236963 A | 10/2009 |
| JP | 3162161 U | 8/2010 |
| JP | 2011113056 A | 6/2011 |
| JP | 2013127496 A | 6/2013 |
| KR | 101231565 B1 | 2/2013 |
| MX | PA02004422 A | 11/2003 |
| MX | PA 02004422 A | 11/2003 |
| PT | 106230 | 9/2013 |
| WO | WO 1994/06109 A1 | 3/1994 |
| WO | WO 1996/042076 A1 | 12/1996 |
| WO | WO 1998/58358 A1 | 12/1998 |
| WO | WO 1999/01074 A1 | 1/1999 |
| WO | WO 2000/36577 A1 | 6/2000 |
| WO | WO 2002/38039 A2 | 5/2002 |
| WO | WO 2002/038039 A3 | 5/2002 |
| WO | WO 2004/032095 A1 | 4/2004 |
| WO | WO 2004/082486 A1 | 9/2004 |
| WO | WO 2005/071639 A1 | 8/2005 |
| WO | WO 2005/083653 A1 | 9/2005 |
| WO | WO 2006/083963 A2 | 8/2006 |
| WO | WO 2007/068360 A1 | 6/2007 |
| WO | WO 2008/021720 A2 | 2/2008 |
| WO | WO 2008/103383 A1 | 8/2008 |
| WO | WO 2009/000939 A1 | 12/2008 |
| WO | WO 2009/089614 A1 | 7/2009 |
| WO | WO 2010/094730 | 8/2010 |
| WO | WO 2010/094730 A1 | 8/2010 |
| WO | WO 2011/035410 A1 | 3/2011 |
| WO | WO 2011/046606 A1 | 4/2011 |
| WO | WO 2011/127379 A2 | 10/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 A1 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2014/197793 A1 | 12/2014 |
| WO | WO 2015/148817 A1 | 10/2015 |
| WO | WO 2016/138528 A1 | 9/2016 |
| WO | WO 2016/183412 A1 | 11/2016 |
| WO | WO 2016/198238 A1 | 12/2016 |
| WO | WO 2016/201085 A1 | 12/2016 |
| WO | WO 2017/031214 A1 | 2/2017 |
| WO | WO 2017/042301 A1 | 3/2017 |

OTHER PUBLICATIONS

European Patent Office, International Search Report for International Application No. PCT/US2011/053859 A3, dated Apr. 5, 2012, entitled "Portable Laparoscopic Trainer," 8 pgs.

European Patent Office, The International Search Report and Written Opinion for International Application No. PCT/US2012/60997, dated Mar. 7, 2013, entitled "Simulated Tissue Structure for Surgical Training," 8 pgs.

European Patent Office, The International Search Report and Written Opinion for International Application No. PCT/US2012/070971, entitled "Advanced Surgical Simulation," dated Mar. 18, 2013, 10 pgs.

Human Patient Simulator, Medical Education Technologies, Inc., http://www.meti.com (1999) all, printed Apr. 12, 2013, 24 pgs.

The International Bureau of WIPO, International Preliminary Report on Patentability and Written Opinion for International Application No. PCT/US2011/053859, titled "Portable Laparoscopic Trainer" dated Apr. 2, 2013, 9 pgs.

(56) References Cited

OTHER PUBLICATIONS

European Patent Office, The International Search Report and Written Opinion for International Application No. PCT/US2013/062363, entitled "Surgical Training Model for Laparoscopic Procedures," dated Jan. 22, 2014, 11 pgs.
European Patent Office, The International Search Report and Written Opinion for International Application No. PCT/US2013/061949, entitled "Surgical Training Model for Laparoscopic Procedures," dated Feb. 17, 2014, 7 pgs.
Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).
European Patent Office, The International Search Report and Written Opinion for International Application No. PCT/US2013/062269, entitled "Surgical Training Model for Transluminal Procedures," dated Feb. 17, 2014, 8 pgs.
European Patent Office, The International Search Report and Written Opinion for International Application No. PCT/US2013/061557, entitled "Surgical Training Model for Laparoscopic Procedures," dated Feb. 10, 2014, 9 pgs.
European Patent Office, The International Search Report and Written Opinion for International Application No. PCT/US2013/061728, entitled "Surgical Training Model for Laparoscopic Procedures," dated Oct. 18, 2013, 9 pgs.
Limps and Things, EP Guildford MATTU Hernia Trainer, http://limbsandthings.com/us/products/tep-guildford-mattu-hernia-trainer/, printed May 29, 2014, 11 pgs.
Simulab, Hernia Model, http://www.simulab.com/product/surgery/open/hernia model, printed printed May 29, 2014, 4 pgs.
McGill Laparoscopic Inguinal Hernia Simulator, Novel Low-Cost Simulator for Laparoscopic Inguinal Hernia Repair, Feb. 8, 2011, 1 pg.
University of Wisconsin-Madison Biomedical Engineering, Inguinal Hernia Model, http://bmedesign.engr.wisc.edu/projects/s10/hernia_model/, printed May 29, 2014, 62 pgs.
The International Bureau of WIPO, International Preliminary Report on Patentability for International Application No. PCT/US2012/070971, titled "Advanced Surgical Simulation" dated Jun. 24, 2014, 7 pgs.
European Patent Office, The International Search Report and Written Opinion of the International Searching Authority for International Application No. PCT/US2014/038195 titled "Hernia Model", dated Oct. 15, 2014, 20 pgs.
European Patent Office, The International Search Report and Written Opinion of the International Searching Authority for International Application No. PCT/US2014/048027 titled "First Entry Model", dated Oct. 17, 2014, 10 pgs.
The International Bureau of WIPO, International Preliminary Report on Patentability for International Application No. PCT/US2012/060997, titled "Simulated Tissue Structure for Surgical Training" dated Apr. 22, 2014, 6 pgs.
European Patent Office, The International Search Report and Written Opinion for International Application No. PCT/US2014/019840, entitled "Advanced Surgical Simulation Constructions and Methods," dated Jul. 4, 2014, 8 pgs.
Kurashima Y et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.
European Patent Office, The International Search Report and Written Opinion for International Application No. PCT/US2014/042998, title; Gallbladder Model, dated Jan. 7, 2015, 20 pgs.
The International Bureau of WIPO, International Preliminary Report on Patentability, for PCT application No. PCT/US2013/053497, titled, Simulated Stapling and Energy Based Ligation for Surgical Training, dated Feb. 12, 2015, 6 pgs.

The International Bureau of WIPO, International Preliminary Report on Patentability for International Application No. PCT/US2013/062363, titled Surgical Training Model for Laparoscopic Procedures, dated Apr. 9, 2015, 9 pgs.
The International Bureau of WIPO, International Preliminary Report on Patentability for International Application No. PCT/US2013/062269, titled Surgical Training Model for Laparoscopic Procedures, dated Apr. 9, 2015, 6 pgs.
The International Bureau of WIPO, International Preliminary Report on Patentability for International Application No. PCT/US2013/061557, titled Surgical Training Model for Laparoscopic Procedures, dated Apr. 9, 2015, 6 pgs.
The International Bureau of WIPO, International Preliminary Report on Patentability for International Application No. PCT/US2013/061728, titled Surgical Training Model for Laparoscopic Procedures, dated Apr. 9, 2015, 7 pgs.
The International Bureau of WIPO, International Preliminary Report on Patentability for International Application No. PCT/US2013/061949, titled Surgical Training Model for Laparoscopic Procedures, dated Apr. 9, 2015, 6 pgs.
The International Bureau of WIPO, International Preliminary Report on Patentability for International Application No. PCT/US2014/019840, titled "Simulated Tissue Structure for Surgical Training" dated Sep. 11, 2015, 8 pgs.
European Patent Office, The International Search Report and Written Opinion for International Application No. PCT/US2015/020574, titled "Advanced First Entry Model for Surgical Simulation," dated Jun. 1, 2015, 12 pgs.
Anonymous: Silicone rubber-from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).
Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.
The International Bureau of WIPO, International Preliminary Report on Patentability for International Application No. PCT/US2014/038195, titled "Hernia Model," dated Nov. 26, 2015, 16 pgs.
The International Bureau of WIPO, International Preliminary Report on Patentability for International Application No. PCT/US2014/042998, titled "Gallbladder Model," dated Dec. 30, 2015, 15 pgs.
European Patent Office, International Search Report and Written Opinion for International Application No. PCT/US2013/053497, titled "Simulated Stapling and Energy Based Ligation for Surgical Training," dated Nov. 5, 2013, 8 pgs.
The International Bureau of WIPO, International Preliminary Report on Patentability for International Application No. PCT/US2014/048027, titled "First Entry Model," dated Feb. 4, 2016, 8 pgs.
European Patent Office, International Search Report and Written Opinion for International Application No. PCT/US2015/059668, titled "Simulated Tissue Models and Methods," dated Apr. 26, 2016, 20 pgs.
Australian Patent Office, Patent Examination Report No. 1 for Australian Application No. 2012358851, titled "Advanced Surgical Simulation," dated May 26, 2016, 3 pgs.
Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2016/032292 titled "Synthetic Tissue Structures for Electrosurgical Training and Simulation," dated Jul. 14, 2016, 11 pgs.
European Patent Office, International Search Report and Written Opinion for International Application No. PCT/US2016/018697 titled "Simulated Tissue Structures and Methods," dated Jul. 14, 2016, 21 pgs.
European Patent Office, International Search Report and Written Opinion for International Application No. PCT/US2016/034591, titled "Surgical Training Model for Laparoscopic Procedures," dated Aug. 8, 2016, 18 pgs.
3D-MED Corporation, "Validated Training Course for Laparoscopic Skills," https://www.3-dmed.com/sites/default/files/product-

(56) References Cited

OTHER PUBLICATIONS additional/product-spec/Validated%20Training%20Course%20for%20Laparoscopie%20Skills.docx_3.pdf , printed Aug. 23, 2016, pp. 1-6.
3D-Med Corporation, "Loops and Wire #1 ," https://www.3-dmed.com/product/loops-and-wire-1 , printed Aug. 23, 2016, 4 pgs.
European Patent Office, The International Search Report and Written Opinion of the International Searching Authority for International Application No. PCT/US2016/036664 titled "Hysterectomy Model", dated Aug. 19, 2016, 15 pgs.
The International Bureau of WIPO, International Preliminary Report on Patentability for International Application No. PCT/US2015/020574, entitled "Advanced First Entry Model for Surgical Simulation," dated Sep. 22, 2016, 9 pgs.
European Patent Office, The International Search Report and Written Opinion of the International Searching Authority for International Application No. PCT/US2016/0043277 titled "Appendectomy Model", dated Oct. 4, 2016, 12 pgs.
European Patent Office, The International Search Report and Written Opinion of the International Searching Authority for International Application No. PCT/US2016/041852 titled "Simulated Dissectible Tissue", dated Oct. 13, 2016, 12 pgs.
Barrier, et al., "A Novel and Inexpensive Vaginal Hysterectomy Simulatory, " Simulation in Healthcare: The Journal of the Society for Simulation in Healthcare, vol. 7, No. 6, Dec. 1, 2012, pp. 374-379.
European Patent Office, Invitation to Pay Additional Fees for International Application No. PCT/US2016/062669, titled "Simulated Dissectible Tissue", dated Feb. 10, 2017, 8 pgs.
European Patent Office, The International Search Report and Written Opinion of the International Searching Authority for International Application No. PCT/US2016/055148 titled "Hysterectomy Model", dated Feb. 28, 2017, 12 pgs.
European Patent Office, Examination Report for European Application No. 14733949.3 titled "Gallbladder Model," dated Dec. 21, 2016, 6 pgs.
European Patent Office, The International Search Report and Written Opinion of the International Searching Authority for International Application No. PCT/US2016/062669 titled "Simulated Dissectible Tissue," dated Apr. 5, 2017, 19 pgs.
European Patent Office, The International Search Report and Written Opinion of the International Searching Authority for International Application No. PCT/US2017/020389 titled "Simulated Tissue Cartridge", dated May 24, 2017, 13 pgs.
The International Bureau of WIPO, International Preliminary Report on Patentability and Written Opinion for International Application No. PCT/US2015/059668, entitled "Simulated Tissue Models and Methods," dated May 26, 2017, 16 pgs.
The International Bureau of WIPO, International Preliminary Report on Patentability for International Application No. PCT/US2016/018697, entitled "Simulated Tissue Structures and Methods," dated Aug. 31, 2017, 14 pgs.
The International Bureau of WIPO, International Preliminary Report on Patentability for International Application No. PCT/US2016/0032292, entitled "Synthetic Tissue Structures for Electrosurgical Training and Simulation," dated Nov. 23, 2017, 2017, 8 pgs.
The International Bureau of WIPO, International Preliminary Report on Patentability for International Application No. PCT/US2016/034591, entitled "Surgical Training Model for Laparoscopic Procedures," dated Dec. 7, 2017, 2017, 14 pgs.
The International Bureau of WIPO, International Preliminary Report on Patentability for International Application No. PCT/US2016/036664, entitled "Hysterectomy Model," dated Dec. 21, 2017, 10 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. EP 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.
The International Bureau of WIPO, International Preliminary Report on Patentability for International Application No. PCT/US2016/055148, entitled "Hysterectomy Model," dated Apr. 12, 2018, 12 pgs.
European Patent Office, The International Search Report and Written Opinion for International Application No. PCT/US2015/022774, entitled "Simulated Dissectible Tissue," dated Jun. 11, 2015, 13 pgs.
The International Bureau of WIPO, International Preliminary Report on Patentability for International Application No. PCT/US2015/022774, titled "Simulated Dissectible Tissue," dated Oct. 6, 2016, 9 pgs.
European Patent Office, The International Search Report and Written Opinion for International Application No. PCT/US2018/018895, entitled "Synthetic Tissue Structures for Electrosurgical Training and Simulation," dated May 17, 2018, 12 pgs.
The International Bureau of WIPO, International Preliminary Report on Patentability for International Application No. PCT/US2016/062669, entitled "Simulated Dissectible Tissue," dated May 31, 2018, 11 pgs.
European Patent Office, The International Search Report and Written Opinion for International Application No. PCT/US2018/018036, entitled "Laparoscopic Training System," dated Jun. 8, 2018, 13 pgs.
European Patent Office, The International Search Report and Written Opinion for International Application No. PCT/US2017/039113, entitled "Simulated Abdominal Wall," dated Aug. 7, 2017, 13 pgs.
European Patent Office, Extended European Search Report for European Patent Application No. EP 18177751.7, titled "Portable Laparoscopic Trainer," dated Jul. 13, 2018, 8 pgs.
European Patent Office, The International Search Report and Written Opinion for International Application No. PCT/US2018/034705, entitled "Laparoscopic Training System," dated Aug. 20, 2018, 14 pgs.
The International Bureau of WIPO, International Preliminary Report on Patentability for International Application No. PCT/US2017/020389, entitled "Simulated Tissue Cartridge," dated Sep. 13, 2018, 8 pgs.
European Patent Office, Extended European Search Report for European Patent Application No. EP 18184147.9, titled "First Entry Model," dated Nov. 7, 2018, 7 pgs.
The International Bureau of WIPO, International Preliminary Report on Patentability for International Application No. PCT/US2017/039113, entitled "Simulated Abdominal Wall," dated Jan. 10, 2019, 8 pgs.
European Patent Office, Extended European Search Report for European Patent Application No. EP 18210006.5, titled "Surgical Training Model for Laparoscopic Procedures," dated Jan. 21, 2019, 7 pgs.
European Patent Office, Extended European Search Report for European Patent Application No. EP 18207214.0, titled "Synthetic Tissue Structures for Electrosurgical Training and Simulation," dated Mar. 28, 2019, 6 pgs.
European Patent Office, Extended European Search Report for European Patent Application No. EP 18216002.8, titled "Surgical Training Model for Laparoscopic Procedures," dated Feb. 4, 2019, 6 pgs.
European Patent Office, Extended European Search Report for European Patent Application No. EP 18216005.1, titled "Surgical Training Model for Laparoscopic Procedures," dated Feb. 4, 2019, 7 pgs.
European Patent Office, Extended European Search Report for European Patent Application No. EP 19159065.2, titled "Simulated Tissue Structures and Methods," dated May 29, 2019, 8 pgs.

(56) References Cited

OTHER PUBLICATIONS

The International Bureau of WIPO, International Preliminary Report on Patentability for International Application No. PCT/US2018/018036, entitled "Laparoscopic Training System," dated Aug. 29, 2019, 8 pgs.

The International Bureau of WIPO, International Preliminary Report on Patentability for International Application No. PCT/US2018/018895, entitled "Synthetic Tissue Structures for Electrosurgical Training and Simulation," dated Sep. 6, 2019, 7 pgs.

European Patent Office, Extended European Search Report for European Patent Application No. EP 20153338.7, titled "Advanced Surgical Simulation Constructions and Methods," dated Mar. 5, 2020, 7 pgs.

European Patent Office, Extended European Search Report for European Patent Application No. EP 19215545.5, titled "Advanced First Entry Model for Surgical Simulation," dated Mar. 26, 2020, 8 pgs.

European Patent Office, Extended European Search Report for European Patent Application No. EP 20158500.7, titled "Surgical Training Device," dated May 14, 2020, 9 pgs.

European Patent Office, Extended European Search Report for European Patent Application No. EP 20186713.2, titled "Simulated Dissectible Tissue," dated Nov. 10, 2020, 12 pgs.

"Surgical Female Pelvic Trainer (SFPT) with Advanced Surgical Uterus," Limbs & Things Limited, Issue 1, Jul. 31, 2003, URL:https://www.accuratesolutions.it/wp-content/uploads/2012/08/ Surgical_Female_Pelvic_Trainer_SFPT_with_Advanced_Uterus_User_Guide.pdf, retrieved Feb. 21, 2020, 2 pgs.

* cited by examiner

SYNTHETIC TISSUE STRUCTURES FOR ELECTROSURGICAL TRAINING AND SIMULATION

CROSS-REFERENCE TO RELATED APPLICATIONS

This application is a continuation of U.S. patent application Ser. No. 15/208,873 entitled "Synthetic tissue structures for electrosurgical training and simulation," filed on Jul. 13, 2016, which is a continuation of International Patent Application No. PCT/US2016/032292 filed on May 13, 2016 entitled "Synthetic tissue structures for electrosurgical training and simulation" which claims priority to and benefit of U.S. Provisional Patent Application No. 62/161,322 filed on May 14, 2015 entitled "Synthetic tissue for electrosurgical training and simulation", and U.S. Provisional Patent Application No. 62/257,877 filed on Nov. 20, 2015 entitled "Synthetic tissue training for electrosurgical training and simulation" all of which are incorporated herein by reference in their entireties.

FIELD OF THE INVENTION

This application relates to synthetic tissue for practicing electrosurgical procedures and, in particular, to conductive synthetic tissue material made from a cross-linked hydrogel and methods of manufacturing such material and synthetic tissue models.

BACKGROUND OF THE INVENTION

Advances in technology have led to an increased use of energy devices in surgical procedures. There is a need for synthetic tissue that closely resembles the response of human tissue to electrosurgery. The synthetic tissue would be advantageous to surgeons and residents for training purposes. The synthetic tissue requires several characteristics to closely resemble human tissue including the ability to be cauterized, cut, and fused when manipulated with energy devices. Additionally, the tissue needs to emulate the mechanical properties of real tissue such as elasticity, toughness, suturability, tactility, color and texture. Furthermore, the material needs to be moldable into a structure that mimics various human organs or membranes for simulating human anatomy. The synthetic tissue may also need to be bondable to a variety of thermoplastics and silicones. The present invention addresses these needs.

SUMMARY OF THE INVENTION

According to one aspect of the invention, a surgical simulator for surgical training is provided. The surgical simulator includes a synthetic tissue structure formed at least in part of a hydrogel including an ionically cross-linked alginate network cross-linked with a covalently cross-linked acrylamide network. The synthetic tissue structure includes at least one of an artificial liver or artificial gallbladder. The at least one of the artificial liver or artificial gallbladder includes at least one lumen substantially formed of a hydrogel including an ionically cross-linked alginate network cross-linked with a covalently cross-linked acrylamide network.

According to another aspect of the invention, a surgical simulator for surgical training is provided. The surgical simulator includes a synthetic tissue structure substantially formed of a hydrogel including an ionically cross-linked alginate network cross-linked with a covalently cross-linked acrylamide network. The synthetic tissue structure includes a first layer formed of the hydrogel having a first ratio of acrylamide to alginate by weight and a second layer formed of the hydrogel having a second ratio of acrylamide to alginate by weight. The second layer is adjacent to the first layer.

According to another aspect of the invention, a surgical simulator for surgical training is provided. The surgical simulator includes a simulated organ model. The simulated organ model includes a first tube having an outer surface and an inner surface defining a first lumen. The first tube is made of a hydrogel comprising a dual interpenetrated network of ionically cross-linked alginate and covalently cross-linked acrylamide having a first ratio of acrylamide to alginate. The simulated organ model includes a second tube having an outer surface and an inner surface defining a second lumen. The second tube is made of a hydrogel comprising a dual interpenetrated network of ionically cross-linked alginate and covalently cross-linked acrylamide having a second ratio of acrylamide to alginate. The first tube is coaxially located inside the second lumen such that the outer surface of the first tube is in contact with the inner surface of the second tube.

According to another aspect of the invention, a method of making a surgical simulator for the practice of electrosurgical techniques is provided. The method includes the steps of providing an acrylamide polymer, providing alginate polymer, providing water, mixing the water with the acrylamide and alginate to form a solution, adding ammonium persulfate to the solution, adding N,N-methylenebisacrylamide to the solution, adding calcium sulfate after the steps of adding ammonium persulfate and adding N,N-methylenebisacrylamide to the solution, casting the solution into a shape representative of an anatomical structure, and curing the solution to form a simulated electrosurgery model made of hydrogel for practicing and simulating electrosurgery.

According to another aspect of the invention, a method of making a surgical simulator for the practice of electrosurgical techniques is provided. The method includes the step of providing an uncured hydrogel including an ionically cross-linked alginate network cross-linked with a covalently cross-linked acrylamide network. The method includes the step of providing a polymer bag, pouring the uncured hydrogel into the polymer bag, sealing the polymer bag, curing the uncured hydrogel inside the polymer bag to form a cured hydrogel, and removing the cured hydrogel. The resulting structure is substantially planar sheet of hydrogel that can be used in building a larger procedural-based surgical training model.

DETAILED DESCRIPTION OF THE INVENTION

Figure 1:
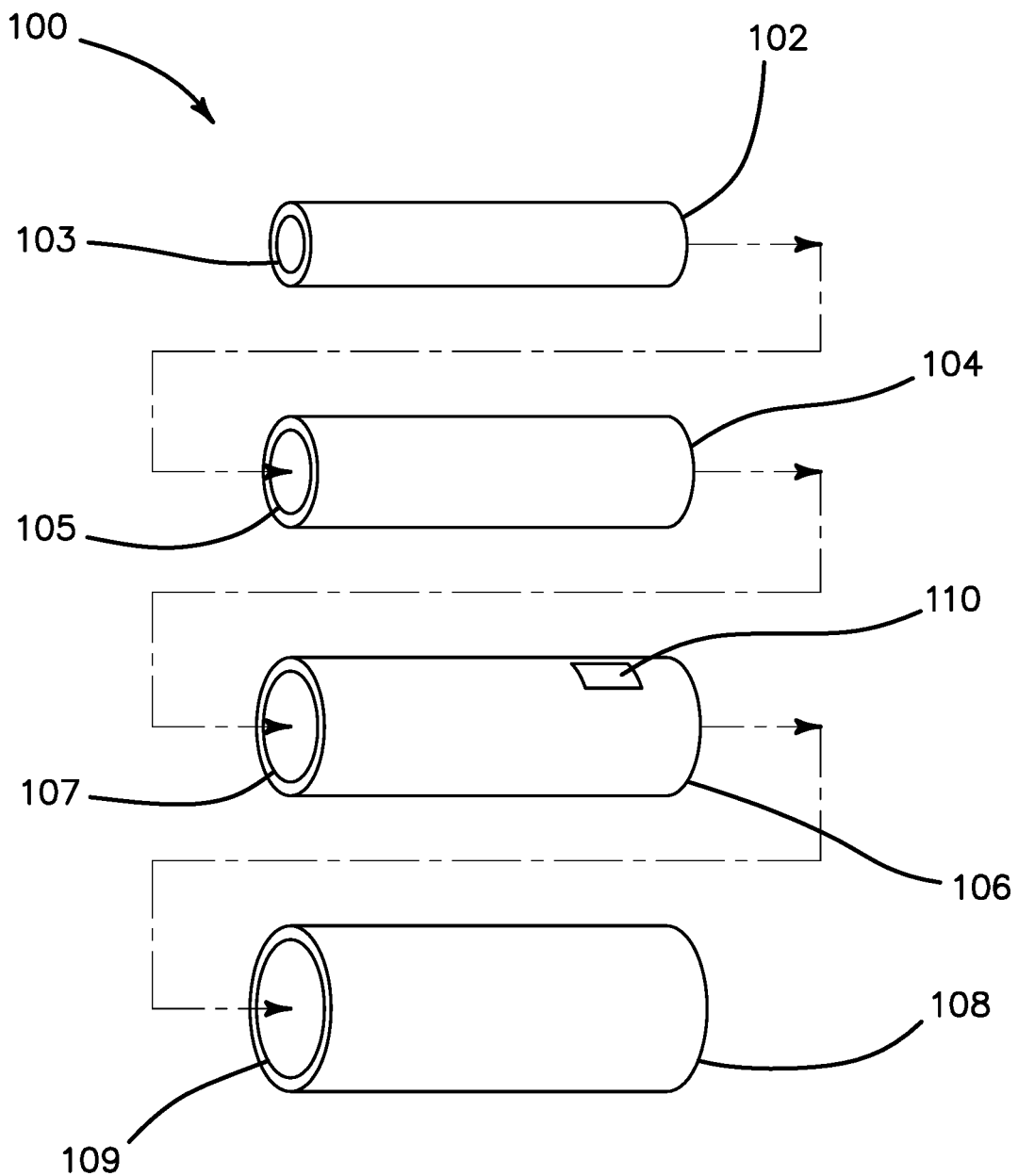
FIG. 1 is an exploded, top perspective view of an organ model according to the present invention.

The material of the present invention is made from a dual interpenetrated cross-linked hydrogel network. The hydrogel is a mixture of two cross-linked polymers: an ionically cross-linked alginate network and a covalently cross-linked polyacrylamide network. The gel material is prepared by mixing an 8:3 ratio of acrylamide to alginate and water. In order to make the organ or tissue parts that are more realistic, color can be incorporated into the process. The colorant is added prior to deionized water being mixed with the acrylamide and alginate solids. Half the water being used to form the gel is used to make the colorant. A wash is created with the water and drops of acrylic paints. The amount and color of paint used varies depending on the organ See Table 1 below for organ color ratios that show how many parts of each color need to be mixed together for a particular organ and/or tissue part. The colored wash is then combined back with the other half of water and mixed with the acrylamide and alginate. Water content of the gel is approximately 86 weight percent. Ammonium persulfate (0.003 the weight of the acrylamide) and N,N-methylenebisacrylamide (0.006 the weight of acrylamide) are added to the solution as a photo initiator and a cross-linker respectively, for the acrylamide. Further, the solution is flushed with argon gas and N,N,N'N'-tetramethylethylenediamine (0.003 the weight of acrylamide) is added under an argon atmosphere as a cross-linking accelerator for the acrylamide. The final additive, calcium sulfate (0.136 weight of alginate), is an ionic cross-linker for the alginate. The slurry is constantly stirred throughout each step until the solution is homogeneous. The gel solution is cast into organ shaped molds and placed in an 85° C. oven for 30 minutes to cure. See the Example below for a specific hydrogel procedure example. To obtain hollow organs, the gel solution can be painted onto a mandrel and placed under a heat lamp to cure. The cured product is a tough, clear hydrogel or colored replica of the organ or tissue. The application of hydrogel organs makes the organ trays for surgical training more dynamic, the trays become more life-like as well as energy device compatible.

In another variation, the material of the present invention is made from a dual interpenetrated cross-linked hydrogel network. The hydrogel is a mixture of two cross-linked polymers: an ionically cross-linked alginate network and a covalently cross-linked polyacrylamide network. The gel material is prepared by mixing an 8:3 ratio of acrylamide to alginate and water. In order to make organs or tissue parts that are more realistic, color can be incorporated into the process. A colorant solution is prepared separate from the acrylamide and alginate mixture to allow for accessibility of different pigments while molding various tissue or organs. The colorant solution is prepared by dissolving acrylic paints in deionized water. The amount and color of paint used varies depending on the organ. See Table I for organ color ratios that show how many parts of each color need to be mixed together for a particular organ and/or tissue part. From the total amount of water used to create the hydrogel, half the water comes from the colorant solution. The colored solution is then combined back with the other half of water which is mixed with the acrylamide and alginate. The total water content of the gel is approximately 86 wt %. Ammonium persulfate (approximately 0.3% the weight of the acrylamide) and N,N-methylenebisacrylamide (approximately 0.6% the weight of acrylamide) are added to the solution as a photoinitiator and a cross-linker respectively, for the acrylamide. Further, the solution is flushed with argon gas for approximately 10-15 minutes in order to displace the air with an inert gas, and then N,N,N'N'-tetramethylethylenediamine (approximately 0.3% the weight of acrylamide) is added under an argon atmosphere as a cross-linking accelerator for the acrylamide. The final additive, calcium sulfate (approximately 13.6% weight of alginate), is an ionic cross-linker for the alginate. The slurry is constantly stirred throughout each step until the solution is homogeneous. The gel solution is cast into organ shaped molds and placed in an 85° C. oven for 60 minutes to cure. See Example below for a specific hydrogel procedure example. To obtain hollow organs, the gel solution can be painted onto a mandrel and placed under a heat lamp to cure. The cured product is a tough, clear hydrogel or colored replica of the organ or tissue. The application of hydrogel organs makes the organ trays for surgical training more dynamic, the trays become more life-like as well as energy device compatible.

Organs and/or tissue made of the hydrogel of the present invention closely resemble and react to manipulation with energy devices similar to the way human organs do. The synthetic tissue made of the hydrogel of the present invention can be cut, cauterized and fused. Two layers of the hydrogel tissue according to the present invention can be separated along a plane using various monopolar and bipolar devices. Furthermore, vessels of the hydrogel can be fused and transected like real blood vessels. Mechanical devices such as scissors, graspers, and sutures can also be used on synthetic tissue made from the hydrogel of the present invention. The tissue has the strength to accommodate sutures and can be further reinforced with mesh to allow additional strength to accommodate sutures in a manner used for actual surgeries without concern for the suture tearing through the synthetic tissue and coming undone. In addition, when wetted the material becomes lubricious and slick making for a life-like feel. The compatibility of the hydrogel with other materials becomes useful when making large assemblies, such as organ trays comprising multiple tissue components for simulators because the synthetic organs not only need to bond to each other, but also are able to bond to the plastic base of the tray. The synthetic organs and tissues made of the hydrogel material should be stored in closed containers with minimal exposure to the atmosphere until ready for use. Due to being predominantly water, the hydrogel material can dry out over time if not stored properly. However, advantageously, the hydrogel of the present invention has the ability to reabsorb water allowing for it to rehydrate after losing moisture and to be used.

In another variation of the present invention, synthetic tissue is made as follows. Sodium metabisulfite is added as an additive to the above mentioned hydrogel. The sodium metabisulfite is added to the solution prior to the calcium sulfate. The amount utilized is equivalent to the amount of ammonium persulfate present in the gel solution. The addition of the sodium metabisulfite allows the gel to be cured at room temperature. Once cast, the hydrogel begins to instantly cure, thus the need for a secondary oven cure is no longer necessary. This process shortens the time required for producing the gel. However, the resulting tissue lacks the same tear strength, elongation, and work time as its oven-cured counterpart.

Another approach utilizes adjusting the ratios of ingredients already present in the hydrogel solution. The two polymers of the hybrid hydrogel are what allow the gel to be elastic and still hold its shape. The 8:3 polymer ratio of acrylamide to alginate in the gel can be adjusted to enhance different properties of the gel. The amount of acrylamide can be increased to increase flexibility and elasticity of the gel; inversely, if the amount of alginate is increased, brittleness is amplified and tear resistance is decreased. The cross-linkers are further responsible for certain characteristics. The cross-linkers essentially entangle the polymer strands together forming a polymer network. Increasing the amount of cross-linkers causes the hydrogel to cure faster and lack elasticity and an insufficient amount of cross-linkers causes the formation of a jelly rather than a gel. The amount of water can also be varied, with the amount of water being inversely proportional to hardness. Gel with higher water content will be softer and will have the formation of a jelly. Ultimately, the ingredients of the hybrid hydrogel can be utilized to enhance different physical and mechanical properties.

Two other examples of replacement hydrogels are an acrylic acid based gel and a clay-based gel. In the acrylic acid hydrogel, an acrylate polymer is created through the polymerization of acrylic acid in an aqueous solution neutralized by sodium hydroxide. A sodium metabisulfite-ammonium persulfate redox reaction acts as an initiator for the polymerization process. The clay based hydrogel is a solution of sodium polyacrylate and clay nanosheets. A dendritic molecular binder (G3-binder) is added to the solution to initiate bonding. The resulting product is a clear, moldable hydrogel.

Besides hydrogel materials semiconductive silicones can be utilized to produce synthetic organs. Semiconductive silicones are silicone rubbers that have been doped with small particles of metal, commonly, nickel-graphite or aluminum. These metal particles essentially make a non-conductive silicone semiconductive by providing a medium for electricity to flow through. Semiconductive silicones are expensive and difficult to bond to other materials. In addition, the silicone needs to contain large amounts of metal particles to provide a short enough arcing distance for the electric current. The above materials and processes can similarly be engaged to manufacture organ trays that are energy compatible.

Figure 2:
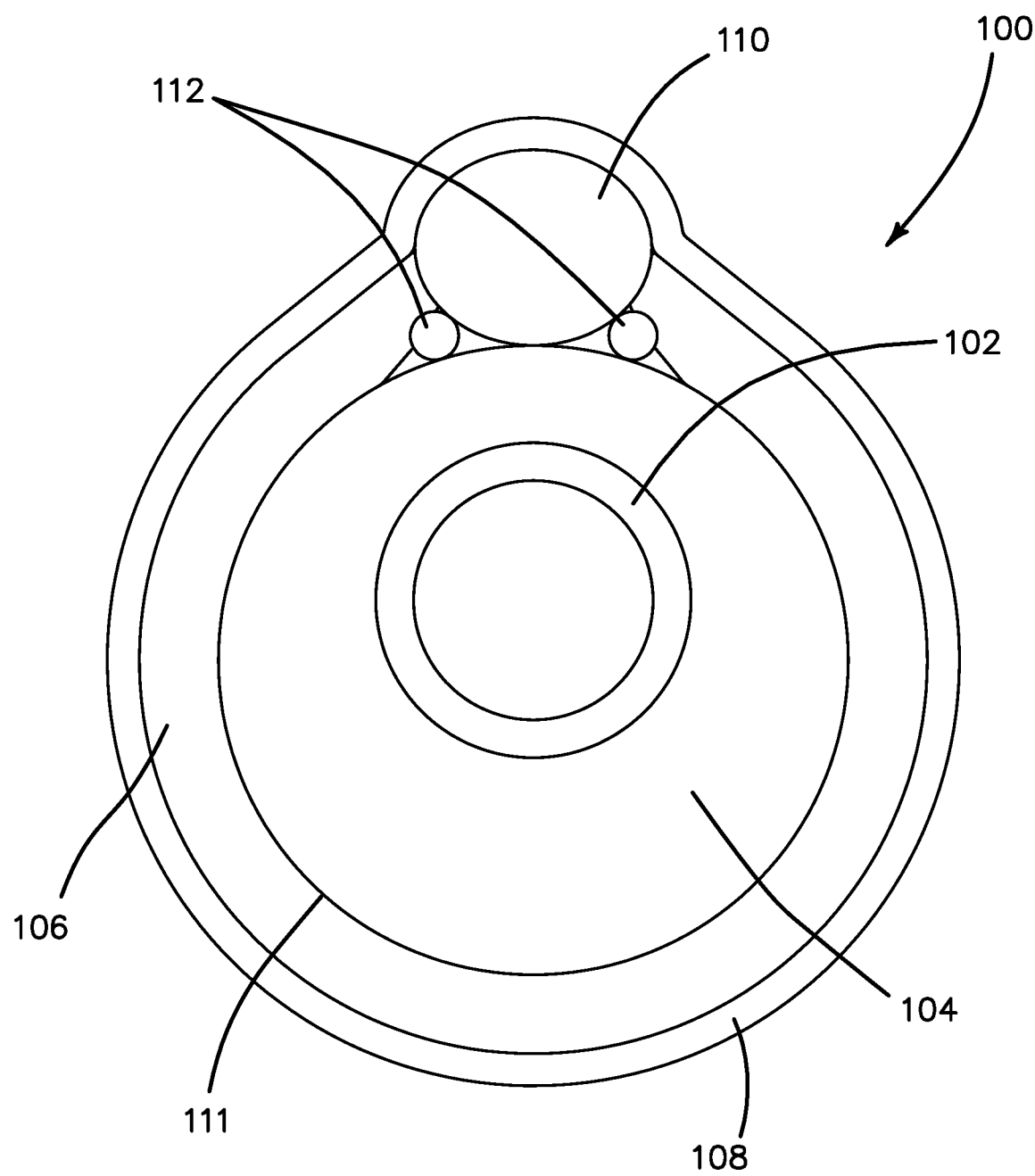
FIG. 2 is a side, cross-sectional view of a rectum model with a simulated prostate system according to the present invention.

An exemplary organ model made of hydrogel material compositions described in this specification is shown in FIGS. 1-3. The organ model is a simulated rectum model 100. The simulated rectum model 100 includes a first tube 102 made of any one of the hydrogel compositions described herein and dyed to have a pink color. In one variation, the hydrogel is selected to have a ratio of approximately 8:1 acrylamide to alginate and approximately 86% water. The first tube 102 defines a first lumen 103 extending between a proximal end and a distal end.

The simulated rectum model 100 further includes a second tube 104 defining a second lumen 105 and extending between a proximal end and a distal end. The second tube 104 is made of yellow dyed hydrogel of any one of the hydrogel compositions described herein. In one variation, the hydrogel is selected to have a ratio of approximately 8:1 acrylamide to alginate and approximately 86% water. The second lumen 105 is dimensioned to receive the first tube 102 inside the second lumen 105 in a concentric-like fashion. The second tube 104 is adhered to the first tube 102 using cyanoacrylate glue. Alternatively, the second tube 104 is cured onto the first tube 102 and no glue is employed. The yellow color of the second tube 104 is selected such that the second tube 104 represents the mesorectum of a human colon.

The model 100 further includes a third tube 106. The third tube 106 defines a third lumen 107. The diameter of the third lumen 107 is dimensioned to receive the second tube 104 inside the third lumen 107 in a concentric fashion. The third tube 106 is adhered to the second tube 104 by being cured on top of the second tube 104. The third tube 106 is made of any one of the hydrogel compositions described herein and dyed to have a yellow and/or orange color to represent a presacral fat layer. In one variation, the hydrogel is selected to have a ratio of approximately 8:1 acrylamide to alginate and approximately 86% water.

The simulated rectum model 100 further includes a fourth tube 108. The fourth tube 108 defines a fourth lumen 109. The diameter of the fourth lumen 109 is dimensioned to receive the third tube 106 inside the fourth lumen 109 in a concentric-like fashion. The fourth tube 108 is made of any one of the hydrogel compositions described herein and dyed to have a pink color. In one variation, the hydrogel is selected to have a ratio of approximately 8:1 acrylamide to alginate and 86% water. The fourth tube 108 is adhered to the third tube 106 with adhesive such as cyanoacrylate glue such as LOCTITE® 401 or 4902 cyanoacrylate glue manufactured by LOCTITE® of Westlake, Ohio. Alternatively, the fourth tube 108 is cured onto the third tube 106 and no adhesive is employed.

In one variation of the simulated rectum model 100, the simulated rectum model 100 further includes a simulated prostate system 110 located and embedded between the third tube 106 and the fourth tube 108. In one variation, the simulated prostate system 110 is located and embedded inside the third tube 106. The simulated prostate system 110 is located at the anterior side of the model 100. The simulated prostate system 110 includes any one or more of the following simulated anatomical structures: simulated prostate, simulated seminal vesicles, simulated bladder, simulated urethra, and simulated vas deferens. The simulated urethra and simulated vas deferens are made of silicone formed into a solid tube or other polymer. The simulated seminal vesicles are made of urethane or other foam overmolded onto the simulated vas deferens. The simulated prostate is made of urethane or other foam overmolded onto the simulated urethra.

In one variation of the simulated rectum model 100, the simulated rectum model 100 further includes one or more collagen layer (not shown) located in any one or more of the following locations: (1) between the second tube 104 and the first tube 102, (2) between the third tube 106 and the second tube 104. The collagen layer is wetted and placed onto the cured hydrogel tube which is then placed in an oven to adhere it. In one variation, the second tube 104 is covered with a thin layer of collagen and the third tube 106 is covered with a thin layer of collagen and electrosurgical dissection takes places between the two adjacent layers of collagen. In another variation, a thin collagen layer is applied to the third tube 106 only and dissection is between the second tube 104 and the collagen layer on the third tube 106. In another variation, a thin first collagen layer is applied to the second tube 104, a thin second collagen layer is applied to the first collagen layer. The prostate system 110 is adhered to the second collagen layer and care is taken to dissect around the prostate system between the first collagen layer and the second collagen layer. In another variation, a thin collagen layer is applied to the prostate system 110 and care is taken to dissect between the second tube 104 and the thin collagen layer to avoid the prostate system 110.

Figure 3A:
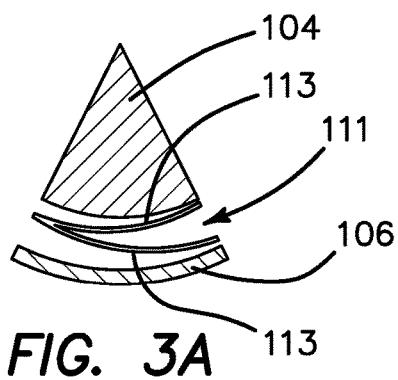
FIG. 3A is posterior, partial, cross-sectional view of two collagen layers located between a second tube and a third tube of a rectum model with according to the present invention.
Figure 3B:
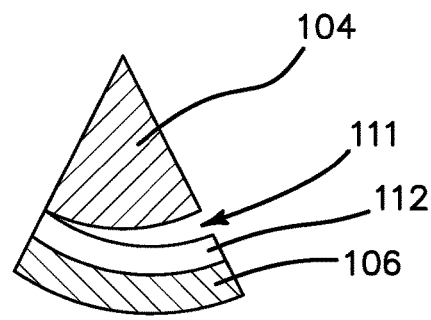
FIG. 3B is a posterior, partial, cross-sectional view of a second tube, third tube and a thin hydrogel layer of a rectum model according to the present invention.
Figure 3C:
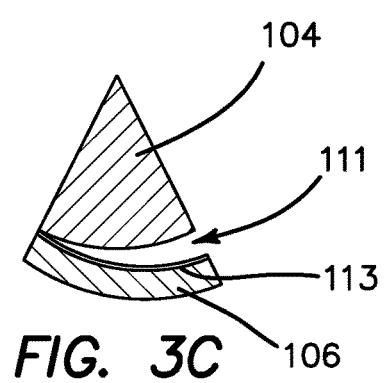
FIG. 3C is a posterior, partial, cross-sectional view of a second tube, third tube and a collagen layer of a rectum model according to the present invention.
Figure 4A:
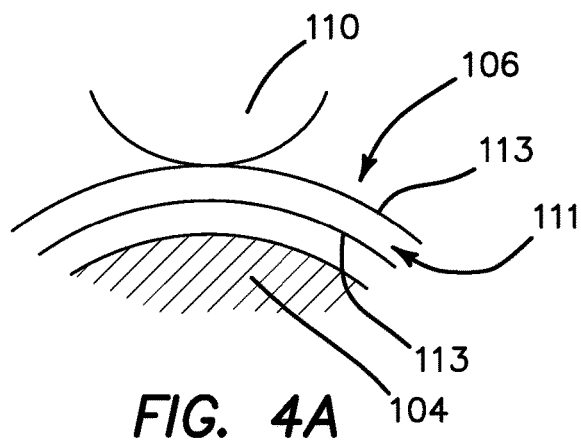
FIG. 4A is an anterior, partial, cross-sectional view of two collagen layers located between a second tube and simulated prostate system of a rectum model according to the present invention.
Figure 4B:
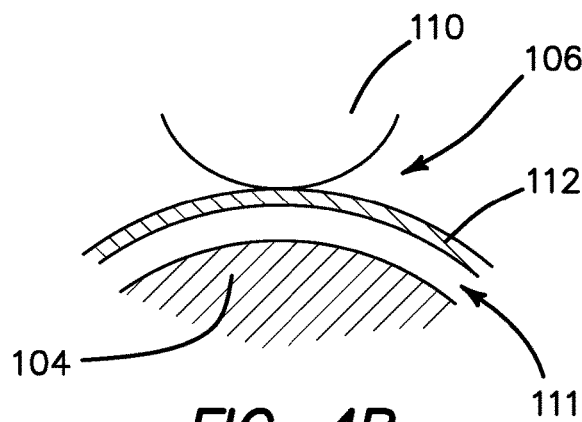
FIG. 4B is an anterior, partial, cross-sectional view of a thin hydrogel layer located between a second tube and simulated prostate system of a rectum model according to the present invention.
Figure 4C:
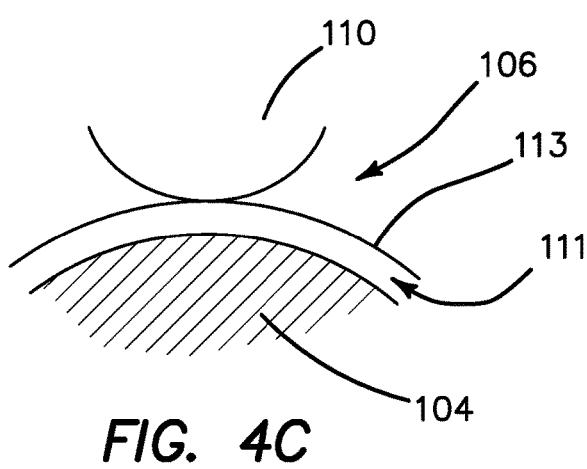
FIG. 4C is an anterior, partial, cross-sectional view of a collagen layer between a second tube and a simulated prostate system of a rectum model according to the present invention.

The simulated rectum model 100 is fantastically suited for practicing transanal total mesorectal excision (TaTME) for cancer located in the lower rectum using electrosurgical devices and electrosurgery techniques. In such a surgical procedure, the cancerous rectum is approached through the anus into the first lumen 103 via a sealable port that is connected to channel. A purse-string suture is tied to seal off the cancerous location of the rectum that includes the tumor. In order to practice this suture technique, the first tube 102 is optionally provided with an embedded mesh layer so that sutures would be held in the first tube 102 and not tear through the hydrogel when pulled. In another variation, the purse-string suture is pre-made during the manufacturing process so that the surgeon can visually locate the suture and only practice techniques subsequent to purse-string suture placement. In the practice of the procedure, the surgeon will commence to dissect in the posterior direction and electrosurgically cut down through first tube 102 and into the second tube 104 which represents the mesorectum and circumferentially around the second tube 104 between the second tube 104 and the third tube 106 being careful not to penetrate into the simulated prostate system 110 and not to penetrate into the fourth tube 108 as can be seen in FIG. 2. Care is also taken not to enter the simulated mesorectum (second tube 104) nor enter into the first tube 102. The user carefully practices to dissect circumferentially around the first tube 102. Exemplary posterior dissection locations and dissection pathways are illustrated in FIGS. 3A-3C. FIG. 3A illustrates a posterior dissection location between the second tube 104 and the third tube 106 and a dissection plane 111 in between two collagen layers 113 if they are employed. FIG. 3B illustrates a posterior dissection location with a dissection pathway between the second tube 104 and the third tube 106, and in particular, between the second tube 104 and a thin hydrogel layer 112 located between the third tube 106 and the second tube 104. FIG. 3C illustrates a posterior dissection location with a dissection pathway 111 between the second tube 104 and a collagen layer 113 adhered to the third tube 106. After dissecting posteriorly, anterior dissection begins by dissecting through the thinner layer of the second tube 104, visible in FIG. 2, until the third tube 106 is reached. Dissection proceeds between the second tube 104 and the third tube 106 along a dissection plane 111 until the posterior dissection is encountered. Exemplary anterior dissection locations and dissection pathways 111 that correspond to posterior dissection pathways 111 of the models configured as shown in FIGS. 3A, 3B and 3C are illustrated in FIGS. 4A, 4B and 4C, respectively. FIG. 4A illustrates an anterior dissection location with a dissection plane 111 lying between two collagen layers 113 if they are provided. FIG. 4B illustrates an anterior dissection location with a dissection plane 111 lying between the second tube 104 and the thin layer of hydrogel 112. FIG. 4C illustrates an anterior dissection location with a dissection plane 111 lying between the second tube 104 and collagen layer 113 if one is provided. Care is taken not to enter the third tube 106 to avoid risk damaging the prostate system 110.

The proximal end of the simulated rectum model 100 may be attached to a transanal adapter. The transanal adapter is a support used to space apart the top cover from the base of a surgical trainer to provide access into the model from the side of the surgical trainer. An example of a surgical trainer is described in U.S. Pat. No. 8,764,452 incorporated by reference herein in its entirety. The transanal adapter includes an opening that is connected to the first lumen of the first tube 102. Surrounding the opening of the transanal adapter, soft silicone is provided to simulate an anus. The practice of the surgical TaTME procedure is performed through the opening of the transanal adapter into the first lumen 103 as described above.

In one variation, the first tube 102 and the second tube 104 are made of hydrogel having a ratio of approximately 8:1 acrylamide to alginate and approximately 86% water and the third tube 106 and the fourth tube 108 are made of hydrogel having a ratio of approximately 8:3 acrylamide to alginate and approximately 86% water. Whereas the intersection of layers/tubes having the same ratio are substantially indistinguishable, the intersection of layers/tubes having different ratios are distinguishable making the intersection plane discernible and more easily separable, leading the practitioner along the correct dissection plane and making dissection easier than if the correct dissection plane was the intersection of layers/tubes having the same ratio.

The simulated rectum model 100 is assembled by first casting the material into hollow tube-like molds that are provided with mandrels. The casting of layers may begin from the innermost layer and proceed to the outermost layer or vice versa. For example, if the casting is to start from the innermost layer, a small tube is filled with material and allowed to cure in an oven. When removed from the small tube mandrel, the cured innermost layer is inserted into a larger diameter tubular mandrel of the desired diameter and the next layer is poured and allowed to cure. The combination is then removed and placed into a tubular mandrel having a larger diameter and the next layer is poured and so forth. Similarly, the model 100 may be constructed beginning with the outer layer and sequentially proceeding to the inner layer. Tubing is placed inside of a larger hollow tubing and the outermost space in between is filled with material until the desired layers is achieved working progressively until the innermost layer is poured. Any layer can be offset from the longitudinal axis to achieve a thicker or thinner layer posteriorly or anteriorly as needed such as for the second tube. If a purse-string suture is to be pre-made, the outer-to-inner manufacturing process would be employed. On the last innermost layer, instead of placing a mandrel in all of the way, material would be cast to completely fill in the rectum except for the top portion. On the top, a small mandrel would be placed allowing only the very top to be hollow. The mandrel could be designed to look like a purse-string, giving the user a visual cue that the purse-string suture has been already completed. To apply a collagen layer, synthetic or natural collagen casing is employed in the form of a sheet or cylinder. If provided in the form of a cylinder, it is cut into sheets. The collagen layer is then soaked in water and water is brushed onto the desired layer of application. The soaked collagen layer is then placed onto the layer of hydrogel. More layers are added as needed and the hydrogel layer and collagen layer are baked together in an oven to adhere the hydrogel to the collagen or the collagen to itself when multiple layers are employed side-by-side. The model 100 is held together by over molding the layers or with cyanoacrylate glue. Silicone components of the model 100 such as the prostate system 110 are adhered to the hydrogel or collagen using cyanoacrylate glue. Urethane molds are employed and the molds may be surface treated with in a variety of ways including but not limited to plasma treating and flame treating to make the mold hydrophilic and improve spreading of hydrogel material into the mold, especially for a hydrogel formulation that does not include sodium metabisulfide. Certain model organ parts, especially thin sheet-like parts such as a simulated peritoneum, are formed by polybag casting. In polybag casting, the hydrogel material is poured into a bag. Any air pockets are pressed out and the bag is sealed and placed between two flat trays. Weights of approximately 2.5-5.0 pounds were laid on top of the trays and allowed to cure into a flat sheet to create an artificial peritoneum or omentum. Artificial vasculature also made of hydrogel may be embedded by arranging the artificial vasculature inside the polybag. Also, smaller hollow molds are utilized to manufacture simulated hollow vessels.

Figure 5:
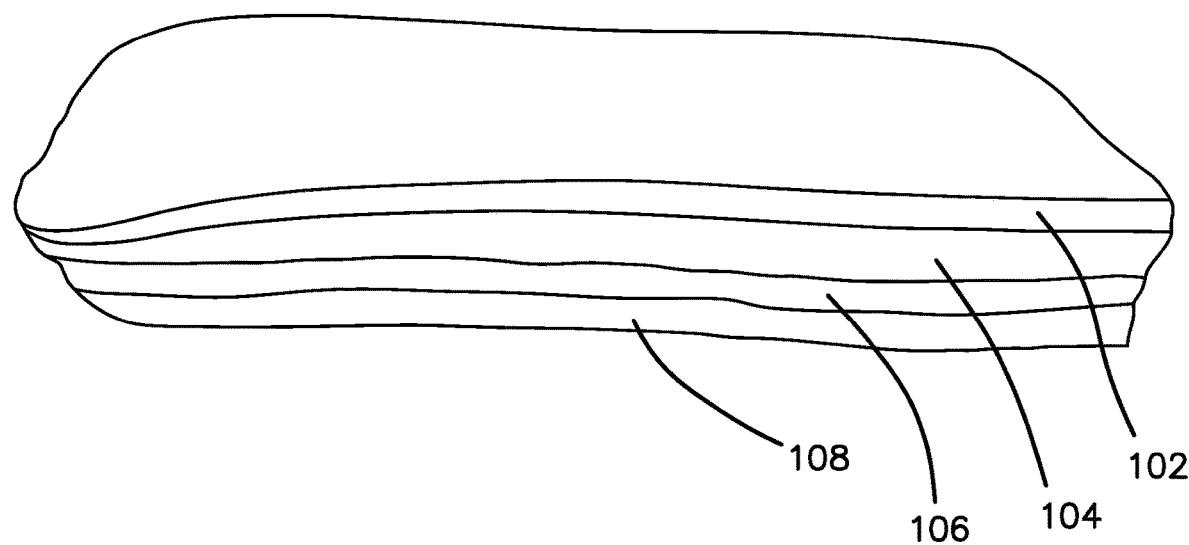
FIG. 5 is a top perspective view of a multi-layered hydrogel according to the present invention.

In another variation, the model 100 does not have a cylindrical shape to represent a rectum. Instead, the model 100 simply includes four layers 102, 104, 106, 108 from top to bottom in the shape of a rectangular or square block as if the cylinder were to be cut open and laid flat as shown in FIG. 5. The block configuration of the layers permits the user to practice the procedures without being confined to a lumen configuration with the procedures performed transluminally. The block allows practitioners to simply practice the electrosurgical techniques in a laparoscopic environment such with the model 100 placed inside a cavity of a surgical trainer between a top cover and a base. In such a variation, the first layer 102 and the second layer 104 are made of hydrogel having a ratio of approximately 8:1 acrylamide to alginate and approximately 86% water and the third layer 106 and the fourth layer 108 are made of hydrogel having a ratio of approximately 8:3 acrylamide to alginate and approximately 86% water.

Any one of the hydrogels disclosed in this specification can be used to form at least part of a simulated tissue structure for the practice of surgical techniques, especially laparoscopic electro-surgical procedures wherein the simulated tissue structure is disposed inside an enclosure substantially enclosing the simulated tissue structure. An example of an enclosure includes a laparoscopic trainer in which a laparoscope is utilized to visualize the surgical field. The simulated tissue structure is not limited to artificial vessels, arteries, veins, one or more organs and tissues, hollow or solid, associated with the human lower rectum as described above and suitable for practicing a TaTME procedure. Also, the TaTME model described above may be made with two layers of hydrogel instead of four layers. In such a model the two layers made of hydrogel include the rectum layer and mesorectum layer, the first tube 102 and the second tube 104, respectively, if the model is formed to have a tubular shape. A variation of such a TaTME model having two layers includes a mesh layer located between the two layers 102, 104. Of course, the TaTME model need not have a tubular shape. Any of the TaTME models may include artificial polyps to be practiced for removal using energy. A gallbladder model may include one or more of an artificial liver, artificial gallbladder, artificial peritoneum, artificial fascia, artificial duct(s), and one or more artificial artery. In an alternative variation of the gallbladder model, the artificial liver is excluded from being made of hydrogel and instead made of silicone or KRATON in order to localize the surge areas to the locations where a simulated procedure would be performed. A simulated tissue structure is substantially made of any one of the hydrogels described herein. In one variation, the simulated tissue structure includes an artificial human ovarian organ that includes one or more of a simulated ovary portion, a uterine horn portion, uterus, ovary, fallopian tube, vagina, cervix, bladder, omentum, and peritoneum. The peritoneum and omentum may further include embedded simulated vasculature, hollow or solid, also made of hydrogel. Other artificial organs that are made of hydrogel and form at least part of a simulated tissue structure include an artificial stomach, kidney, rectum, aorta, tumor, and polyp. Any of the simulated tissue structures made of hydrogel described herein may include a mesh layer. Also, the simulated tissue structure may include two different hydrogels forming different parts of the simulated tissue. For example, as described above, part of a simulated tissue structure may be made with a hydrogel having an 8:3 formulation and another part having an 8:1 formulation. Also, part of a simulated tissue structure may be formed of a hydrogel according to the present invention and part made of silicone or other material and attached, connected, adjacent or in juxtaposition to the part made of hydrogel. For example, in a simulated appendectomy model, an artificial colon is made of silicone and an artificial peritoneum and vessels are made of hydrogel having one or more formulation described herein. In another example, in a simulated gallbladder model the artificial liver is made of silicone or KRATON and all other parts of the gallbladder model are made of hydrogel having one or more formulation described herein. In another example, an artificial rectum is made of silicone and artificial polyps of hydrogel described herein are adhered to the silicone rectum using cyanoacrylate glue.

In use, the simulated tissue structure according to the present invention is configured for use with electrosurgical units, including but not limited to monopolar, bipolar, harmonic or other devices employed in electrosurgery, in order to provide a realistic medium configured into an anatomical portion for the practice of using electrosurgical units, electrosurgical techniques, surgical procedures employing electrosurgical units alone and with other instruments encountered in surgery. The handling of electrosurgical units requires practice as does employing surgical techniques and learning specific procedures performed with the electrosurgical units. When an electrosurgical unit is applied, heat is generated by the electrical current traveling between two polarities in a bipolar system or from one electrical polarity to a ground in a monopolar system. Typically, in a monopolar system, the artificial tissue structure is located above and in contact with a grounding plate/pad which is connected to a ground. In one variation of the simulated tissue structure according to the present invention, that portion of the structure that is composed of hydrogel is placed in direct contact with the grounding pad/plate or other conductive surface. In the event, the entirety of the simulated tissue structure is configured such that the hydrogel is not in direct contact with the grounding pad, a conductive pathway, such as a wire or the like, is provided to contact the hydrogel portion and then pass across non-conductive portions of the model to contact the grounding pad. For example, in a gallbladder model such as the model described in U.S. Patent Application Publication No. US 2014/0370477 to Applied Medical Resources Corporation in California, the anatomical portion is connected to a support in order to permit the model to stand upright. If any one of the liver, peritoneum, gallbladder, vasculature, fascia, duct system or other component of the model is made of hydrogel, a wire is passed into that portion and then fed to contact a metallic frame which is set inside the stand with the frame legs extending all the way through the stand to be exposed at the bottom surface of the stand which then can be place atop a grounding pad. When the hydrogel structure is contacted with an electrosurgical unit, the temperature of the hydrogel structure will increase to a temperature that begins to vaporize the water content of the hydrogel in the location of contact. Because the hydrogel contains approximately 86% water by weight of the hydrogel structure, the model will generate steam that mimics the smoke created during electrosurgery performed on human tissue. Advantageously, the water vapor of the hydrogel structure is not odiferous compared with the smoke produced by real tissue. With prolonged contact with the electrosurgical unit, the water content will be reduced in the location of contact advantageously creating a simulated fusion or seal of tissue typically encountered in real surgery. Hence, the present invention not only advantageously simulates the look and feel of tissue structures that would undergo procedures that employ electrosurgery, but also, responds in manner that mimics real electrosurgery when electrosurgery is applied to the simulated tissue structures. The hydrogel of the present invention can be utilized to simulate dissection of tissue in addition to sealing and/or fusion via an electrosurgical unit.

TABLE 1

| ORGAN | COLOR RATIO |
|---|---|
| Liver | 4 red:1 black |
| Gallbladder | 3 yellow:1 blue |
| Cystic duct | 3 yellow:1 blue |
| Kidney | 4 red:1 blue |
| Spleen | 4 red:1 blue |
| Pancreas | 4 yellow |
| Omentum | 4 yellow:1 white |
| Mesentery | 4 yellow:1 white (serial diluted 8 times) |
| Veins | 3 blue:0.5 black |
| Arteries | 5 red:0.25 black |
| Aorta | 4 red |

EXAMPLE

The following is an example procedure for making a simulated hydrogel liver according to the present invention. In a large glass beaker, add 33.75 g alginate and 90 g acrylamide. Dry mix the two solids until the mixture is uniform. Measure out 614 ml of deionized (DI) water. Add 307 ml (about half) of the 614 ml of DI water to the beaker with the powder mixture. Mix the solution to break apart any alginate adhered to the sides or bottom of the beaker. Once a homogenous solution is formed, maintain the mixing by placing the beaker under an overhead mixer or insert a stir bar and place on stir plate to continue mixing. The remaining 307 ml of water are added to a different beaker and used to prepare the colorant. For a simulated liver, 4 drops of red acrylic paint and 1 drop of black acrylic paint are added to the second jar of DI water and stirred on a stir plate until the water is a uniform color. The now colored 307 ml of DI water is combined back with the other half in the beaker of gel solution. The beaker of gel solution remains mixing on the overhead mixer or stir plate to dissolve all solids and allow for uniform mixing of the colorant. Keep solution stirring and add 0.250 g of ammonium persulfate (APS) and add 0.050 g N,N'-methylenebisacrylamide. Allow the APS and N,N'-MBAA to dissolve in the gel solution prior to proceeding. Hand mix as necessary, since the solution is viscous and the lighter additives will not readily mix with the mixers.

While on the overhead mixer or stir plate, insert a thin hose into the bottom of the beaker of gel solution, the hose should be connected to the argon gas tank. Bubble in a stream of argon gas into the beaker for approximately 15 minutes. Afterwards, remove the hose from the solution and allow hose to sit above the surface and blow a stream of argon gas on top of the gel solution for another 5 minutes. After flushing the solution with argon gas remove the thin hose from the jar. The following step is also completed under argon conditions. Flush the headspace of the N,N,N',N'-tetramethylethylenediamine (N,N,N',N'-TMEDA) bottle with argon. Using a micropipette, pipette 0.290 milliliters of argon gas from the N,N,N',N'-TMEDA bottle head space and eject the gas off to the side, this should be done twice in order to flush the interior of the micropipette. Now, extract 0.290 ml of N,N,N',N'-TMEDA from the bottle using the same micropipette tip and eject into the gel solution. The N,N,N',N'-TMEDA bottle should be sealed quickly after use and stored in a dark area, away from moisture.

Continue stirring, make a slurry of calcium sulfate dihydrate (CaSO4.2H2O) and DI water. Add approximately 25 ml of DI water to 4.59 g of CaSO4.2H2O. Mix thoroughly and add slurry to the hydrogel solution. Wash the remains of the CaSO4.2H2O slurry with DI water and add to the hydrogel solution. Some white clouds may still remain from the addition of the CaSO4.2H2O. These clouds will disappear once hydrogel is cured. Allow gel slurry to mix at medium speed for approximately 1 minute. The gel slurry can now be poured into a liver mold and placed in an oven at 85° C. for 60 minutes to cure the gel. After 1 hour, the mold is removed from the oven and allowed to cool to room temperature. Once cool, the hydrogel liver can be removed from the mold. The final product is a life-like synthetic liver capable of being manipulated with energy devices in addition to mechanical devices.

It is understood that various modifications may be made to the embodiments of the synthetic tissue disclosed herein. Therefore, the above description should not be construed as limiting, but merely as exemplifications of preferred embodiments. Those skilled in the art will envision other modifications within the spirit and scope of the present disclosure.

The invention claimed is:

1. A method of making a surgical simulator, comprising:
providing a solution comprising an acrylamide polymer, an alginate polymer and water;
casting the solution into hollow tube molds;
curing the solution in the hollow tube molds to form hollow tubes made of hydrogel; and
arranging the formed hollow tubes of hydrogel to form a simulated electrosurgery model for practicing and simulating electrosurgery.

2. The method of claim 1 wherein at least one of the hollow tube molds includes a mandrel.

3. The method of claim 1 further comprising providing a colorant and mixing the colorant into the provided solution.

4. The method of claim 1 further comprising flushing the provided solution with argon gas.

5. The method of claim 1 further comprising adding a persulfate to the provided solution.

6. The method of claim 1 wherein the arranging the formed hollow tubes of hydrogel further comprises concentrically placing the formed hollow tubes of hydrogel within each other.

7. The method of claim 6 further comprising providing a collagen layer and placing the collagen layer in between the concentrically placed hollow tubes of hydrogel.

8. The method of claim 1 wherein the arranging the formed hollow tubes of hydrogel further comprises stacking the formed hollow tubes of hydrogel on each other.

9. The method of claim 8 further comprising overmolding the stacked formed hollow tubes of hydrogel.

10. The method of claim 8 further comprising adhering the stacked formed hollow tubes of hydrogel together.

11. A method of making a surgical simulator, comprising:
providing a first solution comprising an acrylamide polymer, an alginate polymer and water;
casting the first solution into a first hollow tube mold;
curing the first solution in the hollow tube molds to form a first hollow tube made of hydrogel;
providing a second solution comprising an acrylamide polymer, an alginate polymer and water;
placing the first hollow tube in a second hollow tube mold;
pouring the second solution over the first hollow tube;
curing the second solution and the first hollow tube to form a simulated electrosurgery model for practicing and simulating electrosurgery.

12. The method of claim 11 further comprising providing a colorant and mixing the colorant into at least one of the provided first solution and second solution.

13. The method of claim 11 further comprising flushing at least one of the provided first solution and second solution with argon gas.

14. The method of claim 11 further comprising adding a persulfate to at least one of the provided first solution and second solution.

15. A surgical simulator for surgical training comprising:
a synthetic tissue model comprising:
a first tube formed of a hydrogel including an alginate network cross-linked with an acrylamide network; and
a second tube formed of a hydrogel including an alginate network cross-linked with an acrylamide network, the first tube having a first diameter larger than a second diameter of the second tube.

16. The surgical simulator of claim 15 wherein the second tube is disposed within the first tube.

17. The surgical simulator of claim 15 wherein the second tube is positioned on the first tube.

18. The surgical simulator of claim 15 further comprising a layer disposed over the first tube, the layer being made of at least one of silicone, mesh, urethane and hydrogel.

19. The surgical simulator of claim 15 further comprising a conductive pathway coupled to the first tube and extending away from the first and second tubes.

20. The surgical simulator of claim 15 wherein the hydrogel of the first and second tubes each has a ratio of acrylamide to alginate by weight, each ratio being the same.

* * * * *